(12) United States Patent
Eichenseher et al.

(10) Patent No.: US 12,226,461 B2
(45) Date of Patent: Feb. 18, 2025

(54) CHIMERIC ENDOLYSIN POLYPEPTIDE, CLUSTER 3B

(71) Applicant: Micreos Pharmaceuticals AG, Baar (DE)

(72) Inventors: Fritz Eichenseher, Baar (DE); Mathias Schmelcher, Baar (DE); Christian Alexander Rohrig, Baar (DE)

(73) Assignee: Micreos Pharmaceuticals AG, Baar (CH)

( * ) Notice: Subject to any disclaimer, the term of this patent is extended or adjusted under 35 U.S.C. 154(b) by 0 days.

(21) Appl. No.: 18/314,864

(22) Filed: May 10, 2023

(65) Prior Publication Data
US 2024/0293517 A1 Sep. 5, 2024

Related U.S. Application Data (62) Division of application No. PCT/EP2023/055393, filed on Mar. 3, 2023.

(30) Foreign Application Priority Data

Mar. 4, 2022 (EP) ..................... 22160212

(51) Int. Cl.
| A61K 38/47 | (2006.01) |
| A61K 8/66 | (2006.01) |
| A61P 31/04 | (2006.01) |
| A61Q 17/00 | (2006.01) |

(52) U.S. Cl.
CPC ............... *A61K 38/47* (2013.01); *A61K 8/66* (2013.01); *A61P 31/04* (2018.01); *A61Q 17/005* (2013.01); *C12Y 302/01017* (2013.01)

(58) Field of Classification Search
None
See application file for complete search history.

(56) References Cited

U.S. PATENT DOCUMENTS 9,789,167 B2 * 10/2017 Loessner ............... A61K 45/06

FOREIGN PATENT DOCUMENTS

WO WO2017046021 A1 3/2017

OTHER PUBLICATIONS

Bamberger et al., "Management of *Staphylococcus aureus* Infections", American Family Physician, vol. 72(12), pp. 2474-2481. (Year: 2005).*
Kuiper, Jesse W. P., et al. "The novel endolysin XZ. 700 effectively treats MRSA biofilms in two biofilm models without showing toxicity on human bone cells in vitro." Biofouling 37.2 (2021): 184-193.
Haddad Kashani, Hamed, et al. "Recombinant endolysins as potential therapeutics against antibiotic-resistant *Staphylococcus aureus*: current status of research and novel delivery strategies." Clinical microbiology reviews 31.1 (2018): e00071-17.
Schmelcher, Mathias, and Martin J. Loessner. "Bacteriophage endolysins: applications for food safety." Current opinion in biotechnology 37 (2016): 76-87.
Eichenseher, Fritz, et al. "Linker-Improved Chimeric Endolysin Selectively Kills *Staphylococcus aureus* In Vitro, on Reconstituted Human Epidermis, and in a Murine Model of Skin Infection." Antimicrobial Agents and Chemotherapy 66.5 (2022): e02273-21.

* cited by examiner

*Primary Examiner* — Michelle F. Paguio Frising
*Assistant Examiner* — Grant C Currens
(74) *Attorney, Agent, or Firm* — N.V. Nederlandsch Octrooibureau (57) ABSTRACT

The invention relates to the field of antibacterial polypeptides, specifically to the field of antibacterial polypeptides having lytic activity for *Staphylococcus*. The invention relates to a novel chimeric endolysin polypeptide specifically targeting a *Staphylococcus* cell. The invention further relates to the use of said chimeric endolysin polypeptide as a disinfectant, as an antimicrobial cosmetic, for detection, such as in a diagnostic application and for medical use, such as for treating an individual suffering from a condition associated with a *Staphylococcus* infection.

13 Claims, 1 Drawing Sheet
Specification includes a Sequence Listing.

```
                           SEQUENCE LISTING

Sequence total quantity: 5
SEQ ID NO: 1            moltype = AA  length = 457
FEATURE                 Location/Qualifiers
REGION                  1..457
                        note = Chimeric polypeptide
source                  1..457
                        mol_type = protein
                        organism = synthetic construct
SEQUENCE: 1
AAQSNHSASW LNNYKKGYGY GPYPLGINGG NHYGVDFFMN VGTPVRAISD GKIVEAGWTN    60
YGGGNEIGLV ENDGVHRQWY MHLSKFNVKV GDRVKAGQII GWSGSTGYST APHLHFQRMT   120
NSFSNNTAQD PMPFLKSAGY GSNSTSSSNN NGLKHIYSNH IKGNKITAPK PSIQGVVIHN   180
DYGSMTPSQY LPWLYARENN GTHVNGWASV YANRNEVLWY HPTDYVEWHC GNQWANANLI   240
GFEVCESYPG RISDKLFLEN EEATLKVAAD VMKSYGLPVN RNTVRLHNEF FGTSCPHRSW   300
DLHVGKGEPY TTTNINKMKD YFIKRIKHYY DGGKLEVSKA ATIKQSDVKQ EVKKQEAKQI   360
VKATDWKTNK YGTLYKSESA SFTPNTDIIT RTTGPFRSMP QSGVLKAGQT IHYDEVMKQD   420
GHVWVGYTGN SGQRIYLPVR TWNKSTNTLG VLWGTIK                           457

SEQ ID NO: 2            moltype = AA  length = 461
FEATURE                 Location/Qualifiers
REGION                  1..461
                        note = Chimeric polypeptide
source                  1..461
                        mol_type = protein
                        organism = synthetic construct
SEQUENCE: 2
AATHEHSAQW LNNYKKGYGY GPYPLGINGG MHYGVDFFMN IGTPVKAISS GKIVEAGWSN    60
YGGGNQIGLI ENDGVHRQWY MHLSKYNVKV GDYVKAGQII GWSGSTGYST APHLHFQRMV   120
NSFSNSTAQD PMPFLKSAGY GKAGGTVTPT PNTGLKHIYS NHIKGNKITA PKPSIQGVVI   180
HNDYGSMTPS QYLPWLYARE NNGTHVNGWA SVYANRNEVL WYHPTDYVEW HCGNQWANAN   240
LIGFEVCESY PGRISDKLFL ENEEATLKVA ADVMKSYGLP VNRNTVRLHN EFFGTSCPHR   300
SWDLHVGKGE PYTTTNINKM KDYFIKRIKH YYDGGKLEVS KAATIKQSDV KQEVKKQEAK   360
QIVKATDWKQ NKDGIWYKAE HASFTVTAPE GIITRYKGPW TGHPQAGVLQ KGQTIKYDEV   420
QKFDGHVWVS WETFEGETVY MPVRTWDAKT GKVGKLWGEI K                      461

SEQ ID NO: 3            moltype = AA  length = 459
FEATURE                 Location/Qualifiers
```

```
REGION                  1..459
                        note = Chimeric polypeptide
source                  1..459
                        mol_type = protein
                        organism = synthetic construct
SEQUENCE: 3
AATHEHSAQW LNNYKKGYGY GPYPLGINGG MHYGVDFFMN IGTPVKAISS GKIVEAGWSN    60
YGGGNQIGLI ENDGVHRQWY MHLSKYNVKV GDYVKAGQII GWSGSTGYST APHLHFQRMV   120
NSFSNSTAQD PMPFLKSAGY GKAGGTVTPT PNTGLKHIYS NHIKGNKITA PKPSIQGVVI   180
HNDYGSMTPS QYLPWLYARE NNGTHVNGWA SVYANRNEVL WYHPTDYVEW HCGNQWANAN   240
LIGFEVCESY PGRISDKLFL ENEEATLKVA ADVMKSYGLP VNRNTVRLHN EFFGTSCPHR   300
SWDLHVGKGE PYTTTNINKM KDYFIKRIKH YYDGGKLEVS KAATIKQSDV KQEVKKQEAK   360
QIVKATDYKT NKYGTLYKSE SASFTANTDI ITRLTGPFRS MPQSGVLRKG LTIKYDEVMK   420
QDGHVWVGYN TNSGKRVYLP VRTWNESTGE LGPLWGTIK                          459

SEQ ID NO: 4            moltype = AA  length = 457
FEATURE                 Location/Qualifiers
REGION                  1..457
                        note = Chimeric polypeptide
source                  1..457
                        mol_type = protein
                        organism = synthetic construct
SEQUENCE: 4
AAQSNHSASW LNNYKKGYGY GPYPLGINGG NHYGVDFFMN VGTPVRAISD GKIVEAGWTN    60
YGGGNEIGLV ENDGVHRQWY MHLSKFNVKV GDRVKAGQII GWSGSTGYST APHLHFQRMT   120
NSFSNNTAQD PMPFLKSAGY GSNSTSSSNN NGLKHIYSNH IKGNKITAPK PSIQGVVIHN   180
DYGSMTPSQY LPWLYARENN GTHVNGWASV YANRNEVLWY HPTDYVEWHC GNQWANANLI   240
GFEVCESYPG RISDKLFLEN EEATLKVAAD VMKSYGLPVN RNTVRLHNEF FGTSCPHRSW   300
DLHVGKGEPY TTTNINKMKD YFIKRIKHYY DGGKLEVSKA ATIKQSDVKQ EVKKQEAKQI   360
VKATDYKTNK YGTLYKSESA SFTANTDIIT RLTGPFRSMP QSGVLRKGLT IKYDEVMKQD   420
GHVWVGYNTN SGKRVYLPVR TWNESTGELG PLWGTIK                            457

SEQ ID NO: 5            moltype = AA  length = 459
FEATURE                 Location/Qualifiers
REGION                  1..459
                        note = Chimeric polypeptide
source                  1..459
                        mol_type = protein
                        organism = synthetic construct
SEQUENCE: 5
AATHEHSAQW LNNYKKGYGY GPYPLGINGG MHYGVDFFMN IGTPVKAISS GKIVEAGWSN    60
YGGGNQIGLI ENDGVHRQWY MHLSKYNVKV GDYVKAGQII GWSGSTGYST APHLHFQRMV   120
NSFSNSTAQD PMPFLKSAGY GKAGGTVTPT PNTGLKHIYS NHIKGNKITA PKPSIQGVVI   180
HNDYGSMTPS QYLPWLYARE NNGTHVNGWA SVYANRNEVL WYHPTDYVEW HCGNQWANAN   240
LIGFEVCESY PGRISDKLFL ENEEATLKVA ADVMKSYGLP VNRNTVRLHN EFFGTSCPHR   300
SWDLHVGKGE PYTTTNINKM KDYFIKRIKH YYDGGKLEVS KAATIKQSDV KQEVKKQEAK   360
QIVKATDWKT NKYGTLYKSE SASFTPNTDI ITRTTGPFRS MPQSGVLKAG QTIHYDEVMK   420
QDGHVWVGYT GNSGQRIYLP VRTWNKSTNT LGVLWGTIK                          459
```

CHIMERIC ENDOLYSIN POLYPEPTIDE, CLUSTER 3B

REFERENCE TO AN ELECTRONIC SEQUENCE LISTING

The contents of the electronic sequence listing (sequence-listing.xml; Size: 9080 bytes; and Date of Creation: May 9, 2023) is herein incorporated by reference in its entirety.

FIELD OF THE INVENTION

The invention relates to the field of antibacterial polypeptides, specifically to the field of antibacterial polypeptides having lytic activity for *Staphylococcus*. The invention relates to a novel chimeric endolysin polypeptide specifically targeting a *Staphylococcus* cell. The invention further relates to the use of said chimeric endolysin polypeptide as a disinfectant, as an antimicrobial cosmetic, for detection, such as in a diagnostic application and for medical use, such as for treating an individual suffering from a condition associated with a *Staphylococcus* infection.

BACKGROUND OF THE INVENTION

The Gram-positive bacteria of the genus Staphylococci are a major concern in human and animal health care, mostly due to the increasing prevalence of antibiotic-resistance. They can infect virtually any tissue, including the skin, soft tissues, bones, the heart, the lung and even the brain (Tong, 2015) and can e.g. be involved in skin disorders and soft tissue infections, such as atopic dermatitis. Additionally, biofilms can serve as centres of infections for systemic infections and sepsis, for example on prosthetic devices and catheters. Among the most prevalent bacterial species are the coagulase-positive *S. aureus* and the coagulase-negative *S. epidermidis*. Infections with Staphylococci are often difficult to treat due to high levels of antibiotics resistance and the physically restricted access to the centres of infection. A problem in e.g. the process of removing *S. aureus* from the skin is the unselective killing of other constituents of the natural microbiota and the undesirable spread of antibiotic resistance. Disinfectants (bleach) and conventional antibiotics are not specific, have broad antimicrobial activity and could also kill beneficial microflora of the skin. Peptidoglycan hydrolases (PGHs) can cleave specific bonds within the peptidoglycan (PG) network of bacteria and have been shown to be active against biofilms. Their high lytic activity makes PGHs potent anti-staphylococcal agents. Endolysins are highly specific, phage-derived PGHs, active against both drug-sensitive and resistant bacteria (Schmelcher et al. 2012). As potential alternatives to antibiotics, they have undergone investigations in vitro, in vivo and are under trial in several clinical studies (Kashani et al. 2017). PGHs of Staphylococci regularly display a domain-like architecture, consisting of enzymatically active domains (EADs) and cell-wall-binding domains (CBDs). The high specificity of staphylococcal PGHs may be attributed to their CBDs, which regularly feature an SH3b-fold. The structures of staphylococcal endolysin SH3b domains have been solved and display great homology to the bacteriocins lysostaphin (LST) and ALE1, suggesting a common recognition site in the PG.

The EADs are more diverse and can be grouped according to their structure and cleavage site within the PG. Cysteine, histidine dependent amidohydrolase/peptidase (CHAP) domains are frequently found in staphylolytic endolysins, for example in phage Twort or phage K. Depending on the CHAP domain present, cleavage can occur at different locations in the PG, including the amide bond of the sugar backbone to the stem peptide and the link of the stem peptide to the peptide cross bridge. Herein, the amidohydrolase/peptidase activity of a CHAP domain is referred to as CHAP activity. M23 domains cleave within the pentaglycine cross-bridge, which connects adjacent stem peptides in the PG of *S. aureus* or cleave between the stem peptide and the pentaglycine cross-bridge. Herein, the peptidase activity of an M23 domain is referred to as M23 peptidase activity or M23 activity. Amidase domains are also frequently found in staphylolytic endolysins, such as in the bacteriophage 2683 endolysin. Amidase domains hydrolyse gamma-glutamyl-containing substrates. Herein, the activity of an amidase domain is referred to as amidase activity.

Major obstacles in the use of endolysins targeting *Staphylococcus* species are low enzyme activity, difficult production in large quantities and/or protein stability. Accordingly, there is an ongoing need for an endolysin polypeptide with improved characteristics on for example antimicrobial activity and stability.

DESCRIPTION OF THE INVENTION

The inventors have established that a novel endolysin polypeptide has inter alia improved activity in view of a benchmark prior art endolysin polypeptide.

Accordingly, in a first aspect there is provided for an endolysin polypeptide that has lytic activity for *Staphylococcus*, said endolysin polypeptide comprising a polypeptide having an amino acid sequence that has at least 86% sequence identity with SEQ ID NO: 1. Preferably, the endolysin polypeptide comprises a polypeptide having an amino acid sequence that has at least 86% sequence identity over the entire length of SEQ ID NO: 1.

An overview of the sequences herein is provided in Table 1.

The endolysin polypeptide is herein interchangeably referred to as the endolysin polypeptide as disclosed herein, the endolysin as disclosed herein, the endolysin polypeptide and the endolysin.

In the embodiments herein, the endolysin polypeptide has at least lytic activity for *Staphylococcus aureus* and may further have lytic activity for *S. delphini, S. hyicus, S. intermedius, S. lutrae, S. pseudintermedius, S. schleiferi* subsp. *Coagulans*, and *S. simulans*. In an embodiment, the endolysin polypeptide has at least lytic activity for *Staphylococcus aureus* and has no lytic activity for *Staphylococcus epidermidis* and/or *Staphylococcus hominis*.

In the embodiments herein, the endolysin polypeptide preferably has increased lytic activity for *Staphylococcus aureus* as compared to the benchmark prior art endolysin polypeptide with the amino acid sequence as set forward in SEQ ID NO: 2. This endolysin polypeptide is herein also referred to as endolysin XZ.700 or XZ.700 and is extensively described in WO2017/046021 which is herein incorporated by reference in its entirety. In WO2017/046021, XZ700 is the polypeptide with the amino acid sequence as set forward in SEQ ID NO: 2.

Lytic activity is herein preferably construed as peptidoglycan hydrolase activity. Lytic activity can be assessed by any suitable method known to the person skilled in the art. Preferably, one of the assays as described in the examples herein is used.

Increased lytic activity is preferably construed as having at least 10%, 20%, 30%, 40%, 50%, 60%, 70%, 80%, 90%, 100%, 200%, 300%, 400%, 500%, 600%, 700%, 800%, 900%, or at least 1000% more activity when assayed under identical conditions. 1000% increase is a 10-fold increase, i.e. 1 log increase. Lytic activity is preferably assayed using the killing assay as described in the examples herein wherein activity is depicted as the amount of reduction of colony forming units (CFU), wherein the reduction is depicted as log reduction in CFU. Preferably, increased activity is assayed using *Staphylococcus aureus* ATC12600 and increased activity is present when at least at one identical concentration of the endolysin polypeptide as disclosed herein, the CFU reduction is at least 0.1 log higher compared to the benchmark endolysin polypeptide XZ.700. In an embodiment, the increased lytic activity is at least 1 log higher CFU reduction when using 125 ng/mL and/or 250 ng/mL endolysin polypeptide as disclosed herein compared to 125 ng/mL or respectively 250 ng/mL of the benchmark endolysin polypeptide XZ.700 in the killing assay as described in the examples herein.

In the embodiments herein, the endolysin polypeptide may have an amino acid sequence that has at least 86% sequence identity with SEQ ID NO: 1. Preferably, the endolysin polypeptide has an amino acid sequence having at least 86% sequence identity over the entire length of SEQ ID NO: 1.

In the embodiments herein, at least 86% sequence identity is preferably construed as at least 86%, 87%, 88%, 89%, 90%, 91%, 92%, 93%, 94%, 95%, 96%, 97%, 98%, at least 99% or 100% sequence identity.

In the embodiments herein, the endolysin polypeptide may have an amino acid sequence that has at least 86% sequence identity with the endolysin polypeptides used in the examples herein.

Accordingly, in the embodiments herein, the endolysin polypeptide may have an amino acid sequence that has at least 86%, 87%, 88%, 89%, 90%, 91%, 92%, 93%, 94%, 95%, 96%, 97%, 98%, at least 99% or 100% sequence identity with SEQ ID NO: 3.

Accordingly, in the embodiments herein, the endolysin polypeptide may have an amino acid sequence that has at least 86%, 87%, 88%, 89%, 90%, 91%, 92%, 93%, 94%, 95%, 96%, 97%, 98%, at least 99% or 100% sequence identity with SEQ ID NO: 4.

Accordingly, in the embodiments herein, the endolysin polypeptide may have an amino acid sequence that has at least 86%, 87%, 88%, 89%, 90%, 91%, 92%, 93%, 94%, 95%, 96%, 97%, 98%, at least 99% or 100% sequence identity with SEQ ID NO: 5.

The person skilled in the art will comprehend that in the embodiments herein, the endolysin polypeptide comprises two or more domains, such as two or three domains; such domains may be separated by a linker, such as a peptide or oligopeptide linker. The peptide linker or oligopeptide linker may be any useful linker known to the person skilled in the art. In an embodiment, the linker comprises or consists of between 5 and 20 amino acids, such as 5, 6, 7, 8, 9, 10, 11, 12, 13, 14, 15, 16, 17, 18, 19 or 20 amino acids. In the embodiments herein, the endolysin polypeptide may comprise one, two, three or more linkers. In an embodiment, the endolysin polypeptide comprises or consists of one M23 domain, one amidase domain and one cell wall binding domain; these domains may be separated by a linker as defined herein.

In the embodiments herein, the length of a polypeptide is in principle not limited, but preferably the length will not be excessively large. Preferably, an endolysin polypeptide as disclosed herein has an overall length not exceeding about 600 amino acids, preferably not exceeding about 500 amino acids, more preferably not exceeding 465, 464, 463, 462, 461, 460, or 459 amino acids.

Further provided is a polynucleotide encoding an endolysin polypeptide as disclosed herein. Said polynucleotide is herein also referred to as a polynucleotide as disclosed herein. The polynucleotide may be any type of polynucleotide know to the person skilled in the art, such as a DNA, an RNA or an mRNA. The polynucleotide may e.g. be a DNA encoding the endolysin polynucleotide which DNA is to be expressed in a host cell or in an in vitro transcription/translation system. The polynucleotide may also be an mRNA to be delivered to a host for in vivo transcription/translation, wherein the host may be a cell or a multicellular organism such as a mammal. Also provided is a nucleic acid construct comprising a polynucleotide as disclosed herein. Said nucleic acid construct is herein referred to as a nucleic acid construct as disclosed herein. Also provided is an expression vector comprising a nucleic acid construct as disclosed herein. Said expression vector is herein referred to as an expression vector as disclosed herein. An expression vector as disclosed herein may be a recombinant expression vector. Such vector may constitute a plasmid, a cosmid, a bacteriophage or a virus, or a part thereof, which is transformed by introducing a nucleic acid construct or a polynucleotide as disclosed herein. Such transformation vectors specific to the host organism to be transformed are well known to those skilled in the art and widely described in the literature. In order to produce a polynucleotide or endolysin polypeptide as disclosed herein in a host, a process for the transformation of a host organism, and integration of a polynucleotide, nucleic acid construct or expression vector as disclosed herein may be appropriate. Such transformation may be carried out by any suitable known means which have been widely described in the specialist literature and are well-known to the person skilled in the art. Also provided is a host cell comprising a polynucleotide as disclosed herein, a nucleic acid construct as disclosed herein or an expression construct as disclosed herein. Said host cell is herein referred to as a host cell as disclosed herein. A host cell as disclosed herein may be any microbial, prokaryotic or eukaryotic, cell which is suitable for expression of the endolysin polypeptide as disclosed herein. Preferably, said cell is an *E. coli*, such as *E. coli* XL1 blue MRF, *E. coli* BL21(DE3).

Further provided is a method for the production of an endolysin polypeptide as disclosed herein comprising:
 culturing a host cell as disclosed herein under conditions conducive to the production of the endolysin polypeptide,
 optionally isolating and purifying the endolysin polypeptide from the culture broth, and
 optionally freeze-drying or spray-drying the endolysin polypeptide.

Preferably, an *E. coli* is used in the method for producing an endolysin polypeptide as disclosed herein. Preferably, an *E. coli* XL1 blueMRF or *E. coli* BL21-Gold(DE3) is used in step i). Preferably, when a His-tag is used, in the step of isolation and purification, IMAC and Econo-Pac Chromatography columns (Biorad) packed with 5 mL low density Nickel chelating agarose beads (ABT beads) in combination with gravity flow are used to purify an endolysin polypeptide as disclosed herein. The eluted polypeptide can be dialyzed for 2, 4, and 12 hours against 3×1l lyophilization buffer, said buffer preferably comprising 50 mM phosphate, 500 mM sucrose, 200 mM mannitol, 0.005% polysorbate20, pH 7.4.

In an embodiment, no His-tag is used; preferably no tag at all is used; accordingly, in an embodiment, the endolysin polypeptide comprises no His-tag or comprises no tag.

Lyophilisation and reconstitution are preferably construed as dehydration by freeze-drying or spray-drying and subsequent reconstitution of the sample by adding water. Preferably, lyophilisation and reconstitution is performed by dialyzing against 3 changes of 300 ml lyophilization buffer (50 mM phosphate or Tris, 500 mM sucrose, 200 mM mannitol, pH 7.4) aliquot and freezing in the gaseous phase of liquid nitrogen. Freeze-drying is preferably performed under standard conditions, preferably at −40° C. and vacuum at 75 mTorr for 60 minutes, followed by increasing the temperature during 5 hours to −10° C. and another 60 minutes at −10° C. at the same vacuum levels. As a final step, the temperature is preferably increased to 25° C. during 10 hours. Spray-drying may be performed using any method known to the person skilled in the art. The endolysin polypeptide is preferably reconstituted by the addition of water.

Further provided is a method for purifying an endolysin polypeptide as disclosed herein with enhanced activity comprising dialysis of an endolysin polypeptide as disclosed herein, said dialysis comprising the steps of:
  i) dialysis against a buffer comprising a chelating compound, and
  ii) dialysis against a divalent metal ion-containing buffer, preferably a divalent metal ion selected from the group consisting of $Co^{2+}$, $Cu^{2+}$, $Mg^{2+}$, $Ca^{2+}$, $Mn^{2+}$ and $Zn^{2+}$.

A "chelating compound" is defined herein as a compound that binds a metal ion. Well known chelating compounds are ethylenediaminetetraacetic acid (EDTA) and ethylene glycol tetraacetic acid (EGTA). Preferably EDTA is used in step i) of the method of the invention.

Preferably, the divalent metal ion of step ii) is selected from the group consisting $Mn^{2+}$, $Co^{2+}$, $Cu^{2+}$, more preferably, said divalent metal ion is selected from the group consisting of $Mn^{2+}$ and $Co^{2+}$, even more preferably said divalent metal ion is $Mn^{2+}$.

It has been demonstrated previously that substituting a divalent metal ion by any of the above defined resulted in an increase of a lytic activity of Ply2638 of 2-2.5 fold. Lytic activity was assessed as described in the examples herein. Preferably, the method leads to an increase in a lytic activity of at least 1.1, 1.2, 1.3, 1.4, 1.5, 1.6, 1.7, 1.8, 1.9 or 2 fold as compared to an untreated polypeptide. Even more preferably, the method leads to an increase in a lytic activity of at least 2.5 fold.

Further provided is a composition comprising an endolysin polypeptide as disclosed herein or a polynucleotide as disclosed herein, or a nucleic acid construct as disclosed herein, or an expression construct as disclosed herein, or a host cell as disclosed herein. Such composition as disclosed herein may comprise a mixture of different polynucleotides, and/or nucleic acid constructs and/or endolysin polypeptides and/or vectors and/or cells as disclosed herein or as obtainable by a method as disclosed herein. Said composition is herein also referred to as a composition as disclosed herein.

In the embodiments herein, the composition may further comprise an excipient acceptable for cosmetics, i.e. an excipient acceptable for cosmetic use. Such excipient acceptable for cosmetics may be any excipient acceptable for cosmetics known to the person skilled in the art, such as but not limited to an emulsifying agent, an emollient, a dye, a colorant, a binder, an anti-foaming agent, a surfactant, a preservative and a film forming agent.

A composition as disclosed herein may further comprise a pharmaceutically acceptable excipient.

Such composition is herein referred to as a pharmaceutical composition and is preferably for use as a medicine or as a medicament. Preferably the medicament is used in the treatment of infectious diseases, preferably infection with a *Staphylococcus*.

Accordingly, further provided is a pharmaceutical composition comprising an endolysin polypeptide as disclosed herein, a polynucleotide as disclosed herein, a nucleic acid construct as disclosed herein, an expression construct as disclosed herein, and/or a host cell as disclosed herein; said pharmaceutical composition further comprising a pharmaceutically acceptable excipient.

A composition, a cosmetic composition or a pharmaceutical composition as disclosed herein may further comprise one or more additional active ingredients. Active preferably defined as showing a lytic activity as defined elsewhere herein. Preferably, said one or more additional active ingredients are selected from the group consisting of a bacteriophage or phage, a phage endolysin derived from such phage and an antibiotic. A phage encompassed herein can be any phage known in literature. Preferably, such phage is, but is not limited, from a family of the list consisting of Myoviridae, Siphoviridae and Podoviridae. Such phage may also be from a family of the list consisting of Tectiviridae, Corticoviridae, Lipothrixviridae, Plasmaviridae, Rudiviridae, Fuselloviridae, Inoviridae, Microviridae, Leviviridae and Cystoviridae. Within the context of the invention, a combination of active ingredients as defined herein can be administered sequentially or simultaneously. A composition of the embodiments herein may be in the liquid, solid or semi-liquid or semi-solid form. It may be an aqueous solution (such as a buffer or a physiological solution), a powder, a suppository, an emulsion, a suspension, a gel, a lotion, a cream, salve, ointment, injectable solution, syrup, spray, inhalant or any other reasonable composition or formulation, a coating composition such as plant coating composition, a stent coating composition, or a catheter coating composition, or a biomaterial such as bone cement.

A composition, cosmetic composition or a pharmaceutical composition as disclosed herein may be used to treat animals, including humans, infected with *Staphylococcus* species as defined herein. Any suitable route of administration can be used to administer said composition including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges.

A composition or pharmaceutical composition as disclosed is preferably said to be active, functional or therapeutically active or able to treat, prevent and/or delay an infectious disease when it decreases the amount of a *Staphylococcus* species present in a patient or in a cell of said patient or in a cell line or in a cell free in vitro system and preferably means that 99%, 90%, 80%, 70%, 60%, 50%, 40%, 30%, 20%, 10%, 5% or less of the initial amount of the *Staphylococcus* species, is still detectable after treatment. Preferably no *Staphylococcus* species is detectable after treatment. Herein, the expression "amount of *Staphylococcus* species" preferably means alive *Staphylococcus* species; the term "alive" is interchangeably used with the term "viable". *Staphylococcus* species may be detected using standard techniques known by the artisan such as immunohistochemical techniques using *Staphylococcus* specific antibodies, tube coagulase tests that detect staphylocoagulase or "free coagulase", detection of surface proteins such as clumping factor (slide coagulase test) and/or protein A (commercial latex tests). Alive *Staphylococcus* species may be detected using standard techniques known by the artisan such as microbiological bacterial culture techniques and/or real-time quantitative reverse transcription polymerase chain reaction to assay for bacterial mRNA. Said decrease is preferably assessed in a tissue or in a cell of an individual or a patient by comparison to the amount present in said individual or patient before treatment with the composition or pharmaceutical composition as disclosed herein. Alternatively, the comparison can be made with a tissue or cell of said individual or patient which has not yet been treated with the composition or pharmaceutical composition as disclosed herein in case the treatment is local.

A composition or pharmaceutical composition as disclosed herein may be administered to a subject in need thereof or to a cell, tissue or organ or said patient for at least one day, one week, one month, six months, one year or more.

Accordingly, there is provided for a composition or a pharmaceutical composition as disclosed herein, for use as a medicament for the treatment of a subject in need thereof. Preferably, the composition or pharmaceutical composition is use as a medicament in the prevention, delay or treatment of a condition in a subject, wherein the condition is associated with infection with a *Staphylococcus*, such as a *Staphylococcus aureus*, Such condition may be but is not limited to a skin infection, soft tissue infections such as infected diabetic foot ulcers, mastitis, pneumonia, meningitis, endocarditis, Toxic Shock Syndrome (TSS), sepsis, septicaemia, bacteraemia, or osteomyelitis. A skin infection may be one selected from the group consisting of pimples, impetigo, boils, furuncles, cellulitis, folliculitis, carbuncles, scaled skin syndrome and abscesses.

Further provided is the composition or a pharmaceutical composition as disclosed herein for use as a medicament, wherein the composition or pharmaceutical composition is for systemic or local administration to the subject.

Further provided is the composition or a pharmaceutical composition as disclosed herein for use as a medicament, wherein the condition is selected from the group consisting of bacteraemia, infective endocarditis, prosthetic joint infection, osteomyelitis, indwelling medical device infection and implanted medical device infection.

Further provided is the composition or a pharmaceutical composition as disclosed herein for use as a medicament, wherein the composition or pharmaceutical composition is for systemic or local administration to the subject and wherein the condition is selected from the group consisting of bacteraemia, infective endocarditis, prosthetic joint infection, osteomyelitis, indwelling medical device infection and implanted medical device infection.

Local administration may e.g. be used during surgery, locally at the site of infection or site of implant. The medical use disclosed herein may be formulated as a product as disclosed herein for use as a medicament for treatment of the stated conditions but can equally be formulated as a method of treatment of the stated conditions using a product as disclosed herein, a product as disclosed herein for use in the preparation of a medicament to treat the stated conditions and use of a product as disclosed herein for the treatment of the stated conditions. Such medical uses are all envisaged by the present invention. The subject in need of treatment, delay and/or prevention of the listed conditions may be any animal subject, preferably a mammal, more preferably cattle, domestic animals like a dog or a cat, or a human subject.

Further provided is a method of cosmetic treatment of the skin of a subject comprising administration, to the skin of the subject, of an endolysin polypeptide as disclosed herein, a polynucleotide encoding such endolysin polypeptide or a composition as disclosed herein. The subject may be any animal subject, preferably a mammal, more preferably cattle, domestic animals like a dog or a cat, or a human subject.

Further provided is the in vitro use of an endolysin polypeptide as disclosed herein or a nucleic acid construct as disclosed herein, or an expression construct as disclosed herein, or a host cell as disclosed herein, or a composition or pharmaceutical composition as disclosed herein, as an antimicrobial, preferably as a food additive or as a disinfectant, preferably for coating or impregnating a medical device. Examples of such use are, but are not limited to, rinsing the cups of a milking device with a composition according to the invention before milking to prevent transmission of Staphylococci from cow to cow, cleaning of surfaces in food industry and cleaning chirurgical tools such as asgastrocameras, peritoneoscopes, thoracoscopes and arthroscopes and medical supplies like catheters and tubes that have long ducts or hollow portions and tend to be repetitively employed by being introduced into the human or animal body. Such use can be combined with any sterilization method or disinfectant known in the art such as ultrasonic cleaning, irradiation or thermal sterilization, by immersing the equipment in a disinfectant solution such as ethanol, ammonium, iodine and/or aldehyde disinfectant, or by using gas sterilization by retaining the device in a closed atmosphere such as formalin gas or ethylene oxide gas.

Further provided is an in vitro method for coating or impregnating a medical device with an endolysin polypeptide as disclosed herein or a composition or a pharmaceutical composition as disclosed herein, comprising contacting the medical device with an endolysin polypeptide as disclosed herein or a composition or pharmaceutical composition as disclosed herein.

Further provided is the use of a an endolysin polypeptide as disclosed herein or a polynucleotide as disclosed herein, or a nucleic acid construct as disclosed herein, or an expression construct as disclosed herein, or a host cell as disclosed herein, or a composition or pharmaceutical composition as disclosed herein, for detecting a *Staphylococcus*, such as *Staphylococcus aureus*, in an ex vivo diagnostic application.

Definitions

"Sequence identity" is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. "Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, MD 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, WI. The aforementioned parameters are the default parameters for amino acid comparisons (along with no penalty for end gaps). Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons. Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A "nucleic acid molecule" or "polynucleotide" (the terms are used interchangeably herein) is represented by a nucleotide sequence. A "polypeptide" is represented by an amino acid sequence. A "nucleic acid construct" is defined as a nucleic acid molecule which is isolated from a naturally occurring gene or which has been modified to contain segments of nucleic acids which are combined or juxtaposed in a manner which would not otherwise exist in nature. A nucleic acid molecule is represented by a nucleotide sequence. Optionally, a nucleotide sequence present in a nucleic acid construct is operably linked to one or more control sequences, which direct the production or expression of said peptide or polypeptide in a cell or in a subject.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject. "Operably linked" may also be used for defining a configuration in which a sequence is appropriately placed at a position relative to another sequence coding for a functional domain such that a chimeric polypeptide is encoded in a cell and/or in a subject.

"Expression" is construed as to include any step involved in the production of the peptide or polypeptide including, but not limited to, transcription, post-transcriptional modification, translation, post-translational modification and secretion.

A "control sequence" is defined herein to include all components which are necessary or advantageous for the expression of a polypeptide. At a minimum, the control sequences include a promoter and transcriptional and translational stop signals. Optionally, a promoter represented by a nucleotide sequence present in a nucleic acid construct is operably linked to another nucleotide sequence encoding a peptide or polypeptide as identified herein.

The term "transformation" refers to a permanent or transient genetic change induced in a cell following the incorporation of new DNA (i.e. DNA exogenous to the cell). When the cell is a bacterial cell, as is intended in the present invention, the term usually refers to an extrachromosomal, self-replicating vector which harbors a selectable antibiotic resistance.

An "expression vector" may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

A "polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

The sequence information as provided herein should not be so narrowly construed as to require inclusion of erroneously identified bases. The skilled person is capable of identifying such erroneously identified bases and knows how to correct for such errors.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 10% of the value.

All patent and literature references cited in the present specification are hereby incorporated by reference in their entirety.

The following examples are offered for illustrative purposes only, and are not intended to limit the scope of the present invention in any way.

Further Embodiments

Further embodiments of the invention are listed here below.
1. An endolysin polypeptide that has lytic activity for *Staphylococcus*, said endolysin polypeptide comprising a polypeptide having an amino acid sequence that has at least 86% sequence identity with SEQ ID NO: 1.
2. An endolysin polypeptide having an amino acid sequence that has at least 86% sequence identity with SEQ ID NO: 1.
3. A polynucleotide encoding the endolysin polypeptide according to embodiment 1 or 2.
4. A nucleic acid construct comprising the polynucleotide according to embodiment 3.
5. An expression vector comprising the nucleic acid construct according to embodiment 4.
6. A host cell comprising the polynucleotide according to embodiment 3, the nucleic acid construct according to embodiment 4 or the expression construct according to embodiment 5.
7. A method for the production of an endolysin polypeptide according to embodiment 1 or 2, comprising:
    culturing a host cell according to embodiment 6 under conditions conducive to the production of the endolysin polypeptide,
    optionally isolating and purifying the endolysin polypeptide from the culture broth, and
    optionally freeze-drying or spray-drying the endolysin polypeptide.
8. A method for producing the endolysin polypeptide according to embodiment 1 or 2 with enhanced activity comprising dialysis of the endolysin according to embodiment 1 or 2, said dialysis comprising the steps of:
    i) dialysis against a buffer comprising a chelating compound, and
    ii) dialysis against a divalent metal ion-containing buffer, preferably a divalent metal ion selected form the group consisting of $Co^{2+}$, $Cu^{2+}$, $Mg^{2+}$, $Ca^{2+}$, $Mn^{2+}$ and $Zn^{2+}$.
9. A composition comprising an endolysin polypeptide according to embodiment 1 or 2, or a polynucleotide according to embodiment 3, or a nucleic acid construct according to embodiment 4, or an expression construct according to embodiment 5, or a host cell according to embodiment 6.
10. A composition comprising an endolysin polypeptide according to embodiment 1 or 2, or a polynucleotide according to embodiment 3, or a nucleic acid construct according to embodiment 4, or an expression construct according to embodiment 5, or a host cell according to embodiment 6, further comprising an excipient acceptable for cosmetics.
11. A pharmaceutical composition comprising an endolysin polypeptide according to embodiment 1 or 2, or a polynucleotide according to embodiment 3, or a nucleic acid construct according to embodiment 4, or an expression construct according to embodiment 5, or a host cell according to embodiment 6, said pharmaceutical composition further comprising a pharmaceutically acceptable excipient.
12. A composition according to embodiment 9, 10 or 11, further comprising an additional active ingredient.
13. A composition according to embodiment 9, 11 or 12, for use as a medicament, preferably for use as a medicament in the treatment of a condition associated with infection with a *Staphylococcus*.
14. A method of treatment of a condition associated with infection with a *Staphylococcus*, comprising administration an endolysin polypeptide according to embodiment 1 or 2, or a polynucleotide according to embodiment 3, or a nucleic acid construct according to embodiment 4, or an expression construct according to embodiment 5, or a host cell according to embodiment 6, or a composition according to embodiment 9, 11 or 12.
15. A method of cosmetic treatment of the skin, comprising administration an endolysin polypeptide according to embodiment 1 or 2, or a polynucleotide according to embodiment 3, or a nucleic acid construct according to embodiment 4, or an expression construct according to embodiment 5, or a host cell according to embodiment 6, or a composition according to embodiment 9, 10 or 12.
16. In vitro use of an endolysin polypeptide according to embodiment 1 or 2, or a polynucleotide according to embodiment 3, or a nucleic acid construct according to embodiment 4, or an expression construct according to embodiment 5, or a host cell according to embodiment 6, or a composition according to embodiment 9 or 10, as an antimicrobial, preferably as a food additive or a disinfectant, preferably for coating or impregnating a medical device.

17. Use of a an endolysin polypeptide according to embodiment 1 or 2 or a polynucleotide according to embodiment 3, or a nucleic acid construct according to embodiment 4, or an expression construct according to embodiment 5, or a host cell according to embodiment 6, or a composition according to any one of embodiments 9 to 12, for detecting a *Staphylococcus*, preferably in a diagnostic application.

FIGURE LEGENDS

FIG. 1

A quantitative killing assay in PBS-T was performed to assess the activity of the endolysin of the invention, three variants thereof and benchmark XZ.700 on *S. aureus* ATCC 12600 (FIG. 1A), *S. epidermidis* BB1336 (FIG. 1B) and *S. hominis* DSM 20328 (FIG. 1C). The concentration-dependent log 10 reduction in viable cell counts was investigated and the average and SEM based on two replicates are depicted. For benchmark XZ.700, the average and SEM based on at least three replicates performed in the same set up are shown for *S. aureus* (FIG. 1A), *S. epidermidis* (FIG. 1B) and *S. hominis* (FIG. 1C).

EXAMPLES

Example 1: Lytic Activity of the Chimeric Endolysin Disclosed Herein

Introduction

*Staphylococcus aureus* is a microbe that is a large problem in modern healthcare. In addition to severe infections of organs and deep tissues, it can be involved in skin disorders and soft tissue infections such as infected diabetic foot ulcers. As part of the natural skin microbiome it colonizes up to 50% of all people. *S. aureus* is considered a causative and aggravating trigger for AD as patients are frequently more colonized with *S. aureus* (approx. 70% of lesional skin) than healthy controls and colonization is increased in more severe cases of AD. A problem in the process of removing *S. aureus* from the skin is the unselective killing of other constituents of the natural microbiota and the undesirable spread of antibiotic resistance. Disinfectants (bleach) and conventional antibiotics are not specific, have broad antimicrobial activity and could also kill beneficial microflora of the skin.

Bacteriophage endolysins are enzymes that specifically bind to the cell wall of bacteria and cleave bonds in the peptidoglycan wall, resulting in bacterial cell death. They can be produced via recombinant technology and only target specific bacterial genera, species, or serovars. Prior art endolysins such as XZ.700 (see in WO2017/046021) have been shown to selectively lyse the bacterial cell wall of *Staphylococcus aureus* species and thereby kill these bacteria, without affecting bacteria of the beneficial microflora, such as *S. epidermidis*. The high specificity against conserved structures of the *S. aureus* cell wall makes resistance induction very unlikely, allowing bacteriophage- and chimeric endolysins to be used for chronic conditions like atopic dermatitis. The objective of this project was to further explore the properties of endolysins since major obstacles in the use of endolysins targeting *Staphylococcus* species are relatively low enzyme activity, difficult production in large quantities and/or protein stability. Accordingly, there is an ongoing need for an endolysin polypeptide with improved characteristics on for example antimicrobial activity and stability.

Materials

TABLE 1

| | | |
|---|---|---|
| here below provides an overview of the sequences herein. | | |
| SEQ ID NO: | Name construct | Sequence |
| 1 | ID203 | AAQSNHSASWLNNYKKGYGYGPYPL GINGGNHYGVDFFMNVGTPVRAISD GKIVEAGWTNYGGGNEIGLVENDGV HRQWYMHLSKFNVKVGDRVKAGQII GWSGSTGYSTAPHLHFQRMTNSFSN NTAQDPMPFLKSAGYGSNSTSSSNN NGLKHIYSNHIKGNKITAPKPSIQG VVIHNDYGSMTPSQYLPWLYARENN GTHVNGWASVYANRNEVLWYHPTDY VEWHCGNQWANANLIGFEVCESYPG RISDKLFLENEEATLKVAADVMKSY GLPVNRNTVRLHNEFFGTSCPHRSW DLHVGKGEPYTTTNINKMKDYFIKR IKHYYDGGKLEVSKAATIKQSDVKQ EVKKQEAKQIVKATDWKTNKYGTLY KSESASFTPNTDIITRTTGPFRSMP QSGVLKAGQTIHYDEVMKQDGHVWV GYTGNSGQRIYLPVRTWNKSTNTLG VLWGTIK |
| 2 | XZ.700 | AATHEHSAQWLNNYKKGYGYGPYPL GINGGMHYGVDFFMNIGTPVKAISS GKIVEAGWSNYGGGNQIGLIENDGV HRQWYMHLSKYNVKVGDYVKAGQII GWSGSTGYSTAPHLHFQRMVNSFSN STAQDPMPFLKSAGYGKAGGTVTPT PNTGLKHIYSNHIKGNKITAPKPSI QGVVIHNDYGSMTPSQYLPWLYARE NNGTHVNGWASVYANRNEVLWYHPT DYVEWHCGNQWANANLIGFEVCESY PGRISDKLFLENEEATLKVAADVMK SYGLPVNRNTVRLHNEFFGTSCPHR SWDLHVGKGEPYTTTNINKMKDYFI KRIKHYYDGGKLEVSKAATIKQSDV KQEVKKQEAKQIVKATDWKQNKDGI WYKAEHASFTVTAPEGIITRYKGPW TGHPQAGVLQKGQTIKYDEVQKFDG HVWVSWETFEGETVYMPVRTWDAKT GKVGKLWGEIK |
| 3 | ID164 | AATHEHSAQWLNNYKKGYGYGPYPL GINGGMHYGVDFFMNIGTPVKAISS GKIVEAGWSNYGGGNQIGLIENDGV HRQWYMHLSKYNVKVGDYVKAGQII GWSGSTGYSTAPHLHFQRMVNSFSN STAQDPMPFLKSAGYGKAGGTVTPT PNTGLKHIYSNHIKGNKITAPKPSI QGVVIHNDYGSMTPSQYLPWLYARE NNGTHVNGWASVYANRNEVLWYHPT DYVEWHCGNQWANANLIGFEVCESY PGRISDKLFLENEEATLKVAADVMK SYGLPVNRNTVRLHNEFFGTSCPHR SWDLHVGKGEPYTTTNINKMKDYFI KRIKHYYDGGKLEVSKAATIKQSDV KQEVKKQEAKQIVKATDYKTNKYGT LYKSESASFTANTDIITRLTGPFRS MPQSGVLRKGLTIKYDEVMKQDGHV WVGYNTNSGKRVYLPVRTWNESTGE LGPLWGTIK |
| 4 | ID165 | AAQSNHSASWLNNYKKGYGYGPYPL GINGGNHYGVDFFMNVGTPVRAISD GKIVEAGWTNYGGGNEIGLVENDGV HRQWYMHLSKFNVKVGDRVKAGQII GWSGSTGYSTAPHLHFQRMTNSFSN NTAQDPMPFLKSAGYGSNSTSSSNN NGLKHIYSNHIKGNKITAPKPSIQG |

TABLE 1-continued here below provides an overview of the sequences herein.

| SEQ ID NO: | Name construct | Sequence |
|---|---|---|
| | | VVIHNDYGSMTPSQYLPWLYARENN GTHVNGWASVYANRNEVLWYHPTDY VEWHCGNQWANANLIGFEVCESYPG RISDKLFLENEEATLKVAADVMKSY GLPVNRNTVRLHNEFFGTSCPHRSW DLHVGKGEPYTTTNINKMKDYFIKR IKHYYDGGKLEVSKAATIKQSDVKQ EVKKQEAKQIVKATDYKTNKYGTLY KSESASFTANTDIITRLTGPFRSMP QSGVLRKGLTIKYDEVMKQDGHVWV GYNTNSGKRVYLPVRTWNESTGELG PLWGTIK |
| 5 | ID190 | AATHEHSAQWLNNYKKGYGYGPYPL GINGGMHYGVDFFMNIGTPVKAISS GKIVEAGWSNYGGGNQIGLIENDGV HRQWYMHLSKYNVKVGDYVKAGQII GWSGSTGYSTAPHLHFQRMVNSFSN |

TABLE 1-continued here below provides an overview of the sequences herein.

| SEQ ID NO: | Name construct | Sequence |
|---|---|---|
| | | STAQDPMPFLKSAGYGKAGGTVTPT PNTGLKHIYSNHIKGNKITAPKPSI QGVVIHNDYGSMTPSQYLPWLYARE NNGTHVNGWASVYANRNEVLWYHPT DYVEWHCGNQWANANLIGFEVCESY PGRISDKLFLENEEATLKVAADVMK SYGLPVNRNTVRLHNEFFGTSCPHR SWDLHVGKGEPYTTTNINKMKDYFI KRIKHYYDGGKLEVSKAATIKQSDV KQEVKKQEAKQIVKATDWKTNKYGT LYKSESASFTPNTDIITRTTGPFRS MPQSGVLKAGQTIHYDEVMKQDGHV WVGYTGNSGQRIYLPVRTWNKSTNT LGVLWGTIK |

Table 2 here below provides an overview of the bacterial strains used in this study.

| Strain | Type | Source |
|---|---|---|
| Staphylococcus aureus | ATCC 12600/ DSM 20231 | Leibniz Institute DSMZ - German Collection of Microorganisms and Cell Cultures GmbH, Germany |
| Staphylococcus epidermidis | BB1336/ RP62A | American Type Culture Collection: ATCC35984 |
| Staphylococcus hominis | DSM 20328 | Leibniz Institute DSMZ - German Collection of Microorganisms and Cell Cultures GmbH, Germany |

Table 3 here below provides an overview of the media to culture the bacterial strains used in the activity assays in this study.

| Medium | Composition | Amount per 1 L | pH | Supplier | Item Nr. |
|---|---|---|---|---|---|
| Tryptic Soy Broth (TSB) | CASO Bouillon powder (Ready mixed) | 30 g | 7.3 | HuberLab | 413820.1210 |
| Luria-Bertani (LB) Agar | Tryptone, Yeast extract, Sodium chloride (Ready mixed) | 40 g | 7.4 | HuberLab | A0927.1000KG |
| LB-PE | Tryptone | 15 g | 7.8 | HuberLab | A1553,1000 |
| | Yeast Extract | 8 g | | HuberLab | 9263.0500 |
| | NaCl | 5 g | | HuberLab | S3014-1KG |

Table 4 here below provides an overview of the buffers used for protein purification and in the activity assays in this study.

| Buffer | Composition | Amount per 1 L | pH | Supplier | Item Nr. |
|---|---|---|---|---|---|
| CIEX PO$_4$ Wash Buffer | 50 mM Na$_2$HPO$_4$ | 7.10 g | 7.4 | Carl Roth | P030.2 |
| | 50 mM NaCl | 2.92 g | | HuberLab | S3014-1KG |
| | 20% Glycerol | 200 ml | | Carl Roth | 3783.5 |
| CIEX PO$_4$ Elution Buffer | 50 mM Na$_2$HPO$_4$ | 7.10 g | 7.4 | Carl Roth | P030.2 |
| | 1M NaCl | 58.44 g | | HuberLab | S3014-1KG |
| | 20% Glycerol | 200 ml | | Carl Roth | 3783.5 |

| Buffer | Composition | Amount per 1 L | pH | Supplier | Item Nr. |
|---|---|---|---|---|---|
| PBS-Tween (PBS-T) | 7 mM Na$_2$HPO$_4$ | 0.99 g | 7.4 | Carl Roth | P030.2 |
| | 3 mM NaH$_2$PO$_4$ (dihydrate) | 0.47 g | | HuberLab | 1.216.771.211 |
| | 130 mM NaCl | 7.60 g | | HuberLab | S3014-1KG |
| | 0.01% Tween-20 | 0.1 ml | | HuberLab | A4974.0500 |
| 10X Stopping Buffer | Trisodium citrate (dihydrate) | 113.75 g | — | Sigma-Aldrich (Merck) | S1804-500G |
| | Citric acid (monohydrate) | 136 g | | Sigma-Aldrich (Merck) | C1909-500G |

Table 5 below provides an overview of the devices used in the activity assays in this study.

| Device | Brand | Supplier | Model | Serial Nr. |
|---|---|---|---|---|
| Spectrophotometer | Thermo Fisher Scientific | Life Technologies | Nanodrop One$^C$ | AZY2017692 |
| FPLC | Cytiva | Cytiva | ÄKTA Pure 25 L | 2587686 |
| Incubator | SalvisLab | Renggli | IC80 | 312.2056/01 |
| Incubator | SalvisLab | Renggli | IC400 | 312.2055/02 |
| Incubator Shaker | Kühner | Renggli | Climo Shaker ISF1-X | 65004.989 |
| Laminar Flow Bench | CleanAir by Baker | Renggli | 4E (Klasse 2) | 19142901-01 |
| −80° C. Chest Freezer | Thermo Fisher Scientific | Renggli | ULT2090-10-V | 300374092 |
| Fridge | Liebherr | Nettoshop | GKv 6410 | 84.994.323.0 |

Methods

The enzymatic activity of the endolysin according to the invention and variants thereof were assessed in quantitative killing assays that were performed in PBS-Tween on three different *Staphylococcus* strains listed in Table 2. As benchmark, XZ.700 was used.

All tested endolysins indicated in Table 1 were produced recombinantly in *E. coli* BL21-Gold(DE3). The bacterial cultures were grown in LB medium optimized for protein expression (LB-PE) supplemented with tetracycline (30 µg/mL) and kanamycin (50 µg/mL) at 37° C. and 180 rpm (Climo Shaker ISF1-X, Kuhner). Once an optical density at 600 nm (OD$_{600nm}$) of 0.5-0.6 was reached (NanoDrop Onec, Thermo Fisher Scientic), the cultures were cooled down on ice. Protein expression was then induced by addition of 0.5 mM IPTG and continued by incubation at 20° C. and 180 rpm for 18 h (Climo Shaker ISF1-X, Kuhner). Following bacterial cell harvest by centrifugation and resuspension in CIEX PO$_4$ wash buffer, cells were lysed using 100 µL of Benzonase (1000U/ml) and a high-pressure cell disrupter (CF1, I&L Biosystems) at 17.5 KPSI. Centrifuged and sterile filtered (0.2 µm, Filtropur S PES-Filter, Sarstedt) lysates were purified by cation exchange chromatography (CIEX) using a 5 mL HiTrap SP FF column (Cytiva) on a fast protein liquid chromatography (FPLC) device (ÄKTA pure, Cytiva). Proteins were eluted with CIEX PO$_4$ elution buffer and the pooled fractions with high protein concentration (NanoDrop One$^C$, Thermo Fisher Scientic) were sterile filtered (0.2 µm, Acrodisc Supor, Pall). Protein identity and purity were confirmed by SDS-PAGE. Protein aliquots were stored at −80° C. and thawed on ice before the start of the assay.

For the quantitative killing assays, the bacterial cultures of *S. aureus* ATCC 12600, *S. epidermidis* BB1336 and *S. hominis* DSM 20328 were incubated overnight in 5 mL TSB at 37° C. and 180 rpm (Climo Shaker ISF1-X, Kuhner). The overnight precultures were diluted 1:25 in 10 mL TSB and grown to mid-log phase (OD$_{600nm}$ of 0.5-0.6) at 37° C. and 180 rpm (Climo Shaker ISF1-X, Kuhner). The bacterial cells were adjusted to have an OD$_{600nm}$ of 0.5±0.02 (NanoDrop One$^C$, Thermo Fisher Scientic) and stored on ice until further use. Endolysin concentrations ranging from 2 µg/mL to 4 ng/mL (2 µg/mL, 1 µg/mL, 500 ng/mL, 250 ng/mL, 125 ng/mL, 62.5 ng/mL, 31.25 ng/mL, 15.63 ng/mL, 7.81 ng/mL, 3.91 ng/mL) were applied to the *Staphylococcus* strains by mixing 100 µL of the 2-fold protein dilutions in PBS-T with 100 µL of OD$_{600nm}$ adjusted bacterial substrates. Bacterial cells mixed with no enzyme but only PBS-T served as negative control. The samples in the 96-multiwell plate were incubated for 2h at 30° C. (IC400, SalvisLab) and thereafter a 5-fold serial dilution was performed in 10-fold diluted stopping buffer to inhibit enzymatic activity. For the viable cell count, 5 µL of each well content was spotted on a square LB agar plate and incubated overnight at 37° C. (IC80, SalvisLab). The dilution series of the incubated *S. hominis* samples, however, was conducted in PBS-T and immediately spotted on a LB agar plate, since the stopping buffer itself showed reducing activity towards *S. hominis* cells. Viable cells from the two lowest possible dilutions of the post incubation dilution series were counted and thereof the concentration-dependent logarithmic reduction of colony forming units were calculated. XZ.700 served as reference endolysin under the same assay conditions as the endolysin according to the invention. For all endolysins, the average CFU reduction and the standard error of the mean (SEM) were calculated based on the performed replicates.

Results

The objective of this study was to assess the enzymatic activity of the endolysin according to the invention and several variants against benchmark endolysin XZ.700, a highly specific *S. aureus* targeting endolysin previously developed (see WO2017/046021).

Figure 1A:
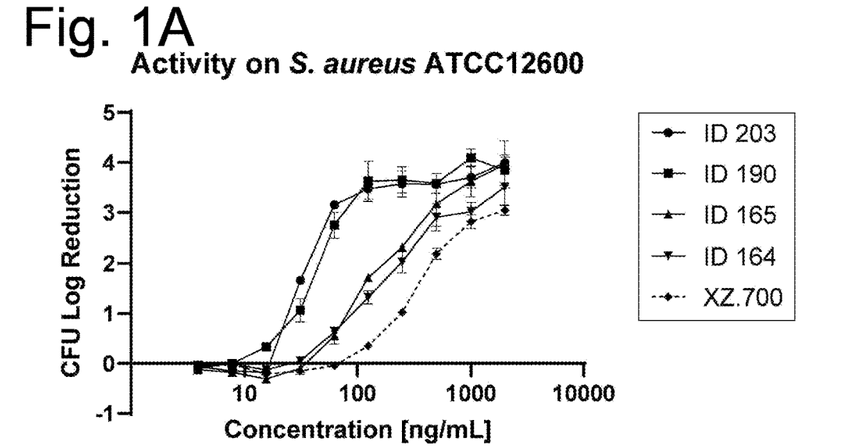
Figure 1B:
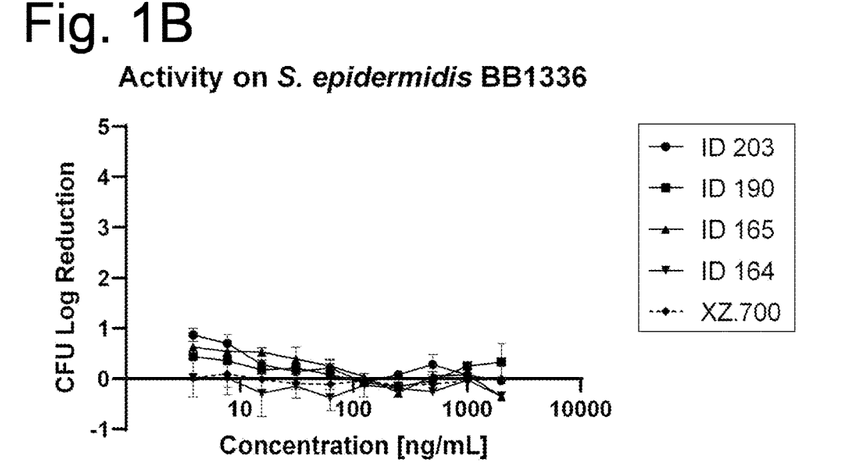
Figure 1C:
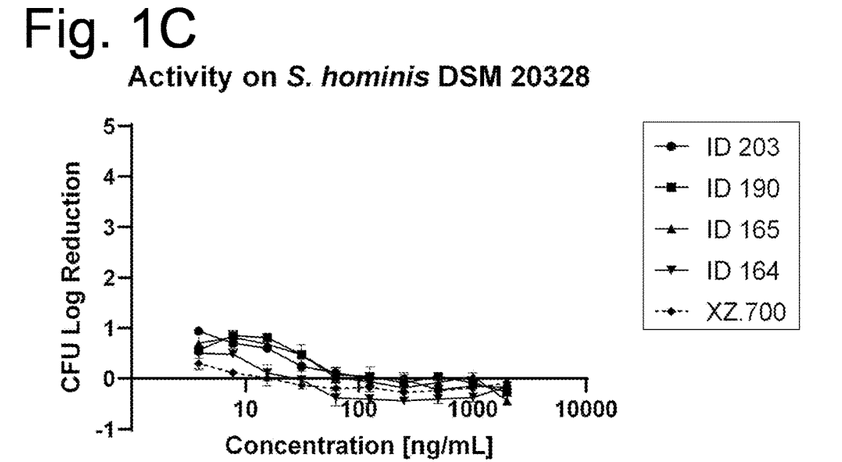

For this purpose, quantitative killing assays (qKA) were performed in PBS-Tween and the capacity of the endolysin to reduce viable bacterial cells of three different staphylococcal strains, in particular *S. aureus* ATCC 12600, *S. epidermidis* BB1336 and *S. hominis* DSM 20328 was assessed. Protein concentrations ranging from 4 ng/mL to 2 µg/mL were applied to $10^6$ CFU/mL viable *Staphylococcus* cells. The average concentration-dependent logarithmic reduction of bacterial numbers was determined based on performance of biological duplicates of the new constructs. The results are depicted in FIGS. 1A, 1B and 1C. Benchmark endolysin XZ.700 was co-tested alongside in all assays.

The endolysin according to the invention demonstrated highly specific killing activity towards *Staphylococcus aureus* (FIG. 1A) whereas no activity was displayed against the other two strains, *Staphylococcus epidermidis* (FIG. 1B) and *Staphylococcus hominis* (FIG. 1C). The CFU counts of all endolysins in the assays on the latter two strains were approximately equal to the negative control, indicating no lysis by the endolysin according to the invention and benchmark XZ.700. Interestingly, the superiority of the endolysin according to the invention over benchmark XZ.700 was more pronounced at lower enzyme concentrations of 62.5 to 250 ng/mL where an increase in killing of *S. aureus* cells of more than two log units was observed. This is evident in FIG. 1A where the curve of the benchmark XZ.700 is concave while the curve of the endolysin according to the invention is convex.

Discussion

The application of endolysin polypeptides with the ability to selectively target *Staphylococcus aureus* without affecting other bacterial species of the natural microflora is highly desirable in numerous skin and deep tissue related infections, mostly due to minimized risk of inducing antibiotic resistance. Prior art endolysins such as XZ.700 (see in WO2017/046021) have been shown to selectively lyse the bacterial cell wall of *Staphylococcus aureus* species and thereby kill these bacteria. In this study, we provide a novel chimeric endolysin polypeptide with improved overall performance. All variants of the novel chimeric endolysin polypeptide demonstrated superiority over XZ.700 by killing two to three log units more of the viable cells compared to XZ.700. This is a surprising and significant improvement in performance.

The data presented herein demonstrates improved and highly selective activity of the newly constructed chimeric endolysin polypeptide compared to the benchmark endolysin in quantitative killing assays.

REFERENCES

Kashani, H. et al., 2017. Recombinant Endolysins as Potential Therapeutics against Antibiotic-Resistant *Staphylococcus aureus*: Current Status of Research and Novel Delivery Strategies. *Clinical Microbiology Reviews*, 31(1).

Schmelcher, M., Donovan, D. M. & Loessner, M. J., 2012. Bacteriophage endolysins as novel antimicrobials. *Future Microbiology*, 7(10), pp. 1147-1171.

Tong, S. Y. C. et al., 2015. *Staphylococcus aureus* Infections: Epidemiology, Pathophysiology, Clinical Manifestations, and Management. *Clinical Microbiology Reviews*, 28(3), pp. 603-661.

The invention claimed is:

1. An endolysin polypeptide that has lytic activity for Staphylococcus, said endolysin polypeptide comprising a polypeptide having an amino acid sequence that has at least 91% sequence identity over the entire length of SEQ ID NO: 5, wherein the endolysin polypeptide has increased lytic activity for Staphylococcus aureus ATCC 12600 at a concentration of 100 ng/ml as compared to the endolysin polypeptide with the amino acid sequence as set forth in SEQ ID NO: 2.

2. The endolysin polypeptide according to claim 1, having an amino acid sequence that has at least 92% sequence identity over the entire length of SEQ ID NO: 5.

3. The endolysin polypeptide according to claim 1, having an amino acid sequence that has at least 93% sequence identity over the entire length of SEQ ID NO: 5.

4. The endolysin polypeptide according to claim 1, having an amino acid sequence that has at least 94% sequence identity over the entire length of SEQ ID NO: 5.

5. The endolysin polypeptide according to claim 1, having an amino acid sequence that has at least 95% sequence identity over the entire length of SEQ ID NO: 5.

6. The endolysin polypeptide according to claim 1, having an amino acid sequence that has at least 96% sequence identity over the entire length of SEQ ID NO: 5.

7. The endolysin polypeptide according to claim 1, having an amino acid sequence that has at least 97% sequence identity over the entire length of SEQ ID NO: 5.

8. The endolysin polypeptide according to claim 1, having an amino acid sequence that has at least 98% sequence identity over the entire length of SEQ ID NO: 5.

9. The endolysin polypeptide according to claim 1, having an amino acid sequence that has at least 99% sequence identity over the entire length of SEQ ID NO: 5.

10. The endolysin polypeptide according to claim 1, having an amino acid sequence that has 100% sequence identity over the entire length of SEQ ID NO: 5.

11. A composition comprising an endolysin polypeptide according to claim 1.

12. A composition according to claim 11, further comprising a pharmaceutically acceptable excipient.

13. A composition according to claim 11, further comprising an additional active ingredient.

* * * * *